United States Patent [19]

Parsons et al.

[11] Patent Number: 5,161,531
[45] Date of Patent: Nov. 10, 1992

[54] METHOD AND APPARATUS FOR INTRAVASCULARLY MEASURING OXIDATIVE METABOLISM IN BODY ORGANS AND TISSUES

[75] Inventors: William J. Parsons, Irving, Tex.; Claude A. Piantadosi; Benjamin J. Comfort, both of Durham, N.C.

[73] Assignee: Duke University, Durham, N.C.

[21] Appl. No.: 846,284

[22] Filed: Mar. 3, 1992

Related U.S. Application Data

[62] Division of Ser. No. 582,756, Sep. 14, 1990.

[51] Int. Cl.$^5$ ................................................ A61B 5/02
[52] U.S. Cl. ..................................... 128/634; 128/665; 128/664
[58] Field of Search ............................... 128/633–634, 128/664–666; 356/41

[56] References Cited

U.S. PATENT DOCUMENTS 4,803,992  2/1989  Lemelson .......................... 128/634

Primary Examiner—Kyle L. Howell
Assistant Examiner—Robert L. Nasser, Jr.
Attorney, Agent, or Firm—Richard E. Jenkins

[57] ABSTRACT

A method and apparatus for measuring oxidative metabolism in an internal organ or tissue of interest wherein a percutaneous intravascular approach is utilized to bring a light-transmitting and receiving scope into contact with the site to be assessed. The tip of the scope is adapted so that the light-transmitting optical fiber(s) and light-receiving optical fiber(s) are in divergent relationship so as to increase the photon pathlength through the tissue of interest to provide optical information from a substantial volume of tissue relative thereto.

12 Claims, 4 Drawing Sheets

METHOD AND APPARATUS FOR INTRAVASCULARLY MEASURING OXIDATIVE METABOLISM IN BODY ORGANS AND TISSUES

RELATED APPLICATION

This application is a divisional application of U.S. Ser. No. 582,756, filed Sept. 14, 1990, and now pending.

1. Technical Field

The present invention relates to a method and apparatus for measuring metabolism in body organs or tissues in vivo, and more particularly to a method and apparatus for delivering and receiving reflected near infrared (NIR) light from an endocardial region of interest by a percutaneous intravascular approach.

2. Related Art

The regional nature of coronary occlusive disease produces a need for a non-invasive means of assessing regional oxidative metabolism in cardiac patients. To those familiar with this art, there is no method presently known of accurately and quickly measuring regional tissue oxygen availability and utilization in human beings. Standard clinical indicators are insensitive to the non-uniform drop-out of myocardial perfusion-metabolism units associated with coronary insufficiency. Radionuclide and angiographic methods permit the evaluation of myocardial perfusion and ventricular wall motion, but the metabolic state of the myocardium cannot be reliably predicted with these methods, particularly in patients with marginal perfusion and/or abnormal ventricular wall motion.

Other methods of measuring myocardial metabolism such as Nuclear Magnetic Resonance Imaging/Spectroscopy and Positron Emission Tomography are costly and require cumbersome pieces of equipment (such as magnets and cyclotrons) which are not compatible with the cardiac catheterization laboratory setting found in most hospitals and/or clinics. The capacity to rapidly discern the metabolic state of the beating human heart, particularly within abnormally contracting myocardial segments, would beneficially affect clinical decisions regarding the need for therapeutic interventions such as blood clot dissolving agents, balloon angioplasty, and coronary artery bypass grafting.

A good review of the prior art spectro-photometric methods for measuring circulatory-respiratory functions, arterial blood oxygenation and blood samples is set forth in U.S. Pat. Nos. 4,223,680 and 4,281,645 to Jobsis. The application of differential spectroscopy using near infrared (NIR) light in blood perfused body organs was discovered by Jobsis as described in detail in the aforementioned patents.

Jobsis emphasized in both of his patents that near infrared (NIR) light must span a relatively long path (e.g. several centimeters) in length in order for his invention to work. The long pathlength is significant in that it allows the light photons to travel deeply into the tissue of interest so that the received optical signal will contain information from a substantial volume of tissue. Also, the longer pathlength minimizes the light-scattering effects of structures which are superficial to the region of interest. Since, as shown in FIG. 2 of U.S. Pat. No. 4,223,680, the backscattered light from superficial structures may not contain metabolic information of interest, and may obscure detection of the desired metabolic information, a method was sought by Jobsis to minimize this biophysical effect. Accordingly, both Jobsis patents teach that the near infrared (NIR) light must be transmitted to the test organ (in situ) and then the radiation intensity must be detected and measured at a point spaced-apart from the point of light entry. As indicated in FIG. 1 and FIG. 2 of U.S. Pat. No. 4,223,680, the physical distance between entrance and exit of near infrared (NIR) light is specified to be several centimeters.

Applicants believe that the disclosure in the Jobsis patents is correct in its contention that the light detector fiber bundle must be spaced-apart from the light source fiber bundle to minimize light scattering from superficial tissue regions. Moreover, applicants have discovered in their experiments that the bundles should also be spaced-apart even if the light source fiber bundle and light detector fiber bundle are oriented parallel to each other as suggested by Abe in U.S. Pat. No. 4,513,751. Simply transmitting near infrared (NIR) light down one optical fiber and receiving the reflected light with a second optical fiber which is parallel and immediately adjacent to the transmitting fiber, as proposed by Abe for visible light wavelengths, will not permit the desired accurate near infrared (NIR) measurement of oxidative metabolism within a substantial tissue volume.

Summarily, it is highly desirable for intravascular application of a red to near-infrared (NIR) light sending and receiving device that a single scope containing both the transmitting and receiving optical fibers be used to acquire optical information from an endocardial site. The introduction of two separate send and receive scopes by a percutaneous, intravascular approach to the endocardium would be hampered by motion artifact of the heating myocardial wall and the instability of the optical alignment of the two scopes relative to the tissue region of interest. Applicants have overcome the shortcomings of the prior art as disclosed in the Jobsis and Abe patents and developed a steerable fiber optic device described hereinbelow which delivers and receives near infrared (NIR) light through a single small-diameter scope (less than 3.3 mm in diameter) positioned at the endocardial surface by means of a percutaneous intravascular approach which is applicable in a standard clinical catheterization laboratory. The procedure using applicants' device can be done as part of a routine diagnostic catheterization study, and permits the measurement of regional myocardial oxygenation from within the beating heart.

DISCLOSURE OF THE INVENTION

In accordance with the present invention, applicants provide an apparatus and method for measuring tissue oxygen availability and utilization in internal body organs such as the heart, brain, liver and kidneys or selected body tissue. The invention contemplates inserting a tube containing a plurality of optical fibers through at least a portion of the length of a body conduit and into contact with the organ or tissue of interest wherein the tube comprises at least one light-transmitting optical fiber and at least one light-receiving optical fiber. Light is directed into the light-transmitting optical fiber so that the light will be transmitted therethrough and into the organ or tissue of interest in a direction divergent from the light-receiving optical fiber. Reflected light which has traversed a portion of the organ or tissue of interest is received in the light-receiving optical fiber and is transmitted therethrough. Finally, the reflected light is analyzed to obtain measurements of tissue oxygenation and/or related data for the organ or tissue of interest. The light-transmitting optical fiber is optically connected to a multi-wavelength spectrometer, and the light-receiving optical fiber is optically connected to a photodetector. Although the specific features of the invention will become apparent from the detailed disclosure hereinbelow, applicants wish to note that the divergent path of red and near infrared (NIR) light from the light-transmitting optical fiber and through the tissue of interest and back to the light-receiving optical fiber increases the light photon pathlength through the tissue of interest so as to provide optical information from a substantial volume of tissue and to minimize undesirable backscatter of light from superficial tissue layers.

It is therefore an object of the present invention to overcome the above-noted drawbacks of the related art and to provide a novel method and apparatus for accurately measuring oxygen availability and utilization at a designated body organ or tissue region of interest in vivo.

Another object of the present invention is to provide a method and apparatus for measuring oxygen availability and utilization of a designated body organ or tissue by means of a percutaneous, intravascular approach thereto.

Another object of the present invention is to provide a photometric reflectance apparatus and method of use which utilizes a single tube for transmitting and receiving near infrared (NIR) light from a body organ or tissue of interest in contact with the distal end of the tube.

Still another object of the present invention is to provide an apparatus and method for accurately measuring oxygen availability and utilization of a designated organ or tissue by minimizing undesirable backscatter of light from superficial tissue layers.

Yet another object of the present invention is to provide an apparatus and method for accurately measuring oxygen availability and utilization of a designated organ or tissue wherein the photons of near infrared (NIR) light travel a relatively long path without requiring the use of spaced-apart light-sending and light-receiving optical fiber bundles.

Some of the objects of the invention having been stated, other objects will become evident as the description proceeds, when taken in connection with the accompanying drawings described below.

BEST MODE FOR CARRYING OUT THE INVENTION

Figure 1:
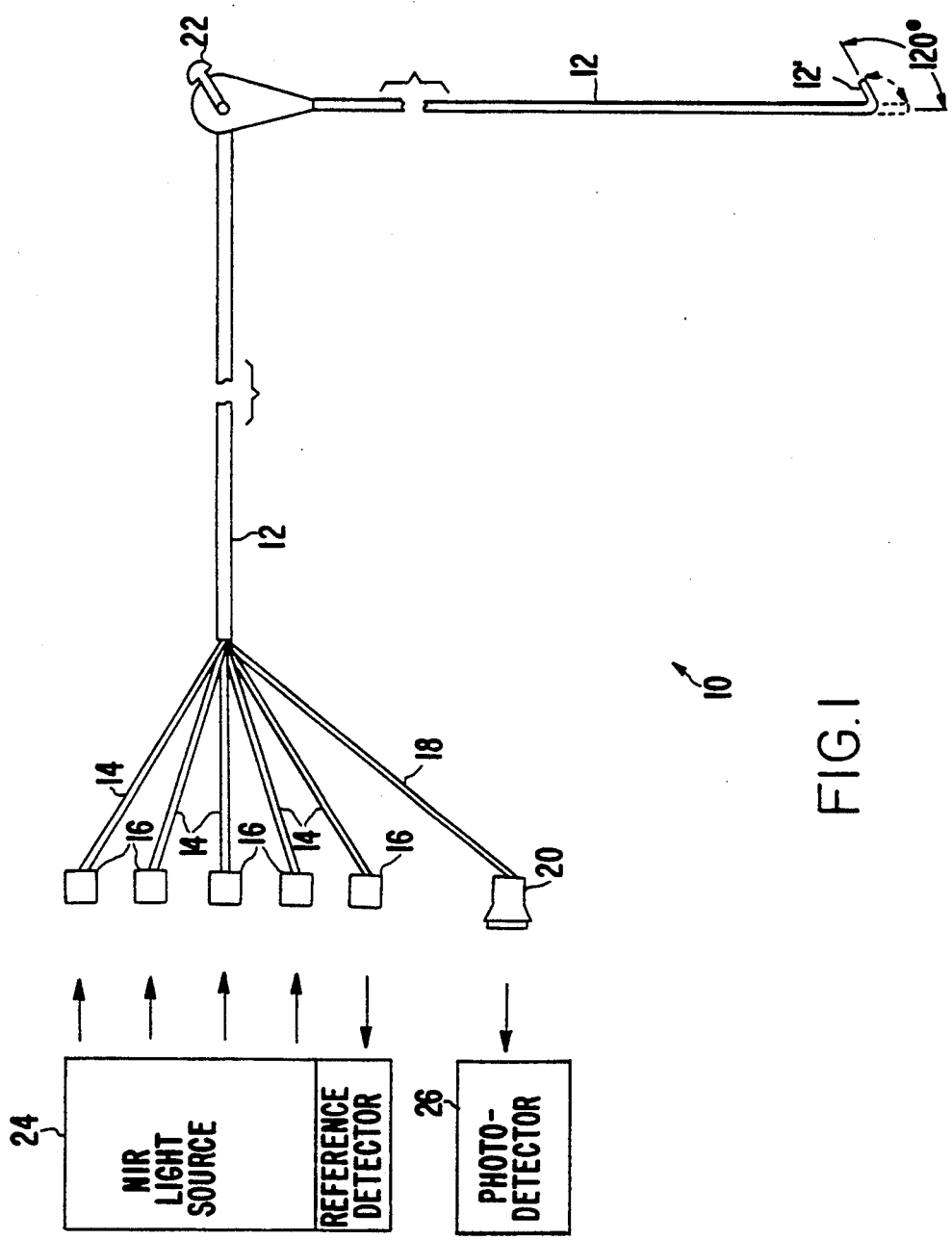
FIG. 1 is a schematic side view showing an apparatus for conducting a method of the present invention.

Referring now to the drawings, a first embodiment of the apparatus of the invention is shown in FIG. 1 and generally designated 10. Device 10 comprises an elongated tube 12, most suitably formed from a flexible plastic sheathing, which serves as a conduit or casing for a plurality of light-transmitting optical fibers 14 which terminate at their proximal end in polished optical coupling connectors 16. Also contained within tube 12 are a plurality of light-receiving optical fibers 18 which terminate at their proximal end in polished optical coupling connector 20. A steering apparatus 22 is positioned generally at a medial portion of the length of tube 12 and serves to manipulate the steerable tip 12' of elongate flexible tube 12. The medial position of the steering apparatus allows manipulation of the apparatus and its steerable tip under sterile conditions. Most suitably, a 2 cm length of the steerable tip 12' is capable of being bent through an arc of 120° by steering apparatus 22 (see FIG. 1).

The light-transmitting optical fibers 14 of device 10 will most suitably be evenly and randomly distributed to one or more optical coupling connectors 16 with one connector 16 connecting to the reference reflectance detector and the remaining one or more optical connectors 16 used for sending near infrared (NIR) light from one or more different wavelength near infrared (NIR) light sources 24. The light-receiving optical fibers 18 will transmit received light along the length of device 10 to optical connector 20 and photodetector 26. The proximal ends of all optical fibers 14 and 18 are ground and polished at their respective optical connectors 16 and 20, for optimal optical coupling with the near infrared (NIR) light source and reference detector 24 and photodetector 26.

Figure 2:
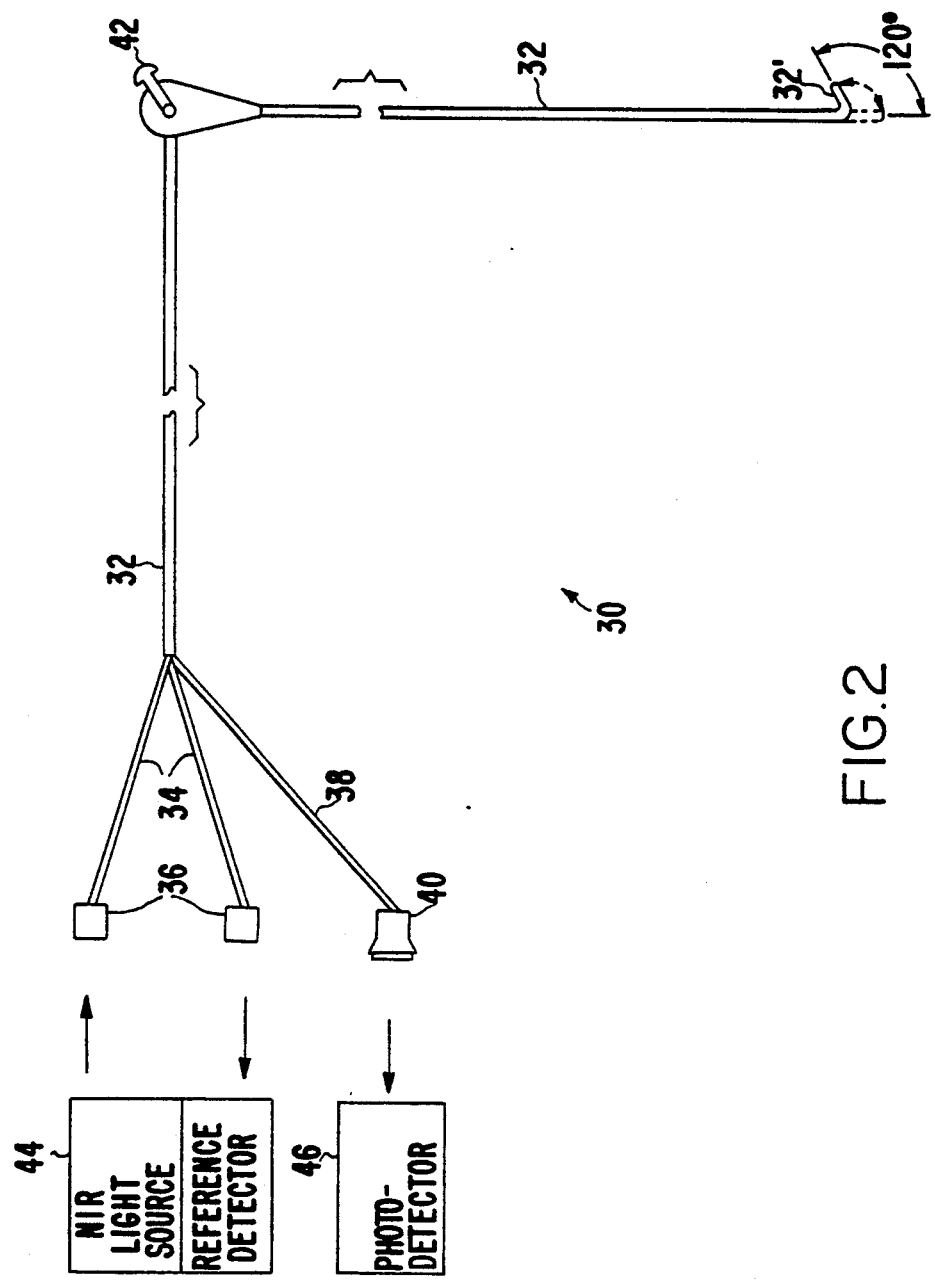
FIG. 2 is a side elevation of another embodiment of an apparatus for conducting a method of the present invention.

Although device 10 of FIG. 1 provides for four different near infrared (NIR) light transmissions from near infrared (NIR) light source 24, FIG. 2 of the drawings schematically illustrates a second embodiment 30 of the device of the invention wherein the different near infrared (NIR) light transmissions are transmitted within tube 32 along light-transmitting optical fibers 34 on a time-shared basis. Accordingly, the number of light-transmitting optical fibers can be reduced by a significant number as best seen with reference to FIG. 2 wherein light-transmitting optical fibers 34 terminate into two optical coupling connectors 36. One connector is optically connected to light source 44, which provides the different wavelength pulsed light transmissions on a time-shared basis, and a second optical coupling connector 36 which connects the reference reflectance detector. Tube 32 of device 30 also contains light-receiving optical fibers 38 which terminate at their proximal end in optical coupling connector 40 which is optically associated with photodetector 46. Steering apparatus 42 is utilized to manipulate steerable tip 32' as in the device shown in FIG. 1.

Most suitably, the outer diameter of both tubes 12 and 32 of devices 10 and 30, respectively, which extend from the steering apparatus to the steerable tips do not exceed 3.3 mm (10 French) so that a percutaneous intravenous use of the device of the invention is practical. Also, the length of the sections of tubes 12 and 32 from the steering apparatus to the steerable tips should be at least 150 cm in order to permit access to the heart chambers by the femoral arterial/venous intravascular approach. The length of tubes 12 and 32 from the optical coupling connectors to steering apparatus 22 and 42, respectively, should be at least 2 meters in order to permit the manipulation of the steering apparatus under sterile conditions.

Figures 3A, 3B, 3C:
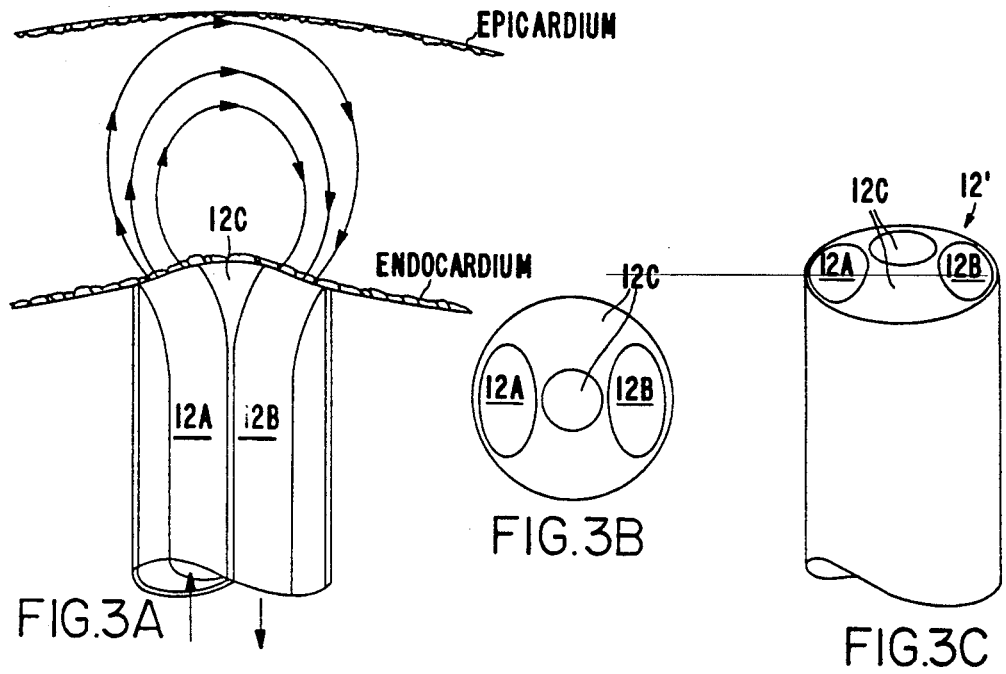
FIGS. 3A-3C are side, top, and perspective views, respectively, of the conical tip of the optical fiber carrying tube utilized in the apparatus of the invention.
Figures 4A, 4B, 4C:
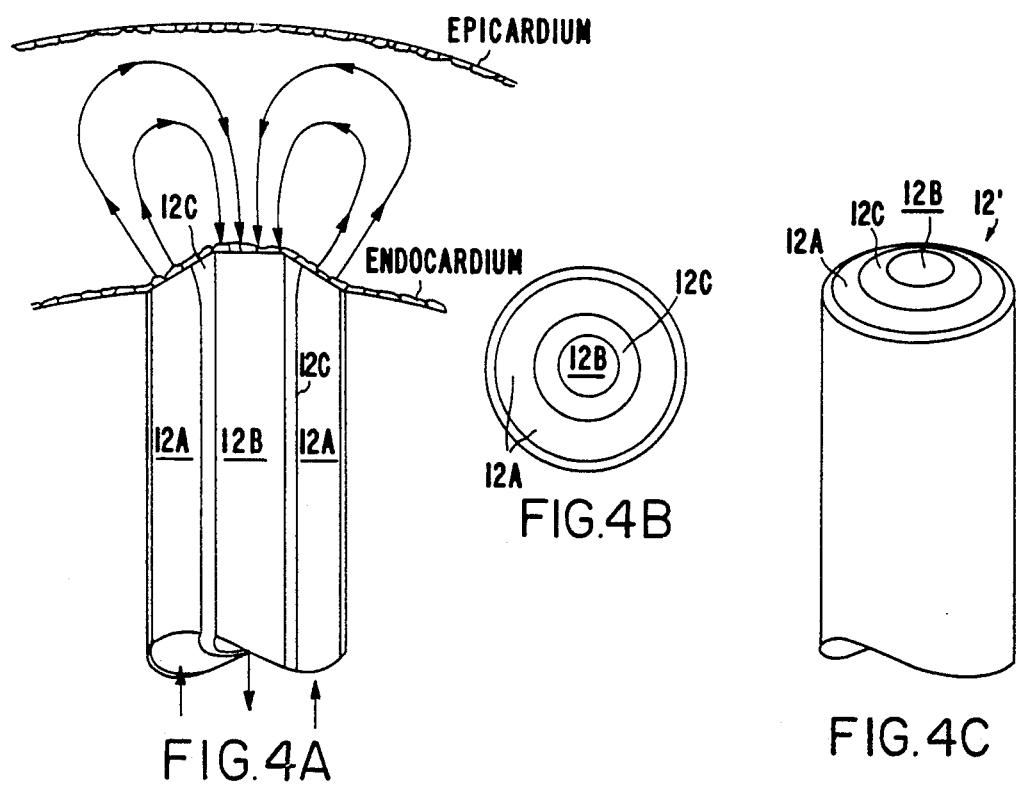
FIGS. 4A-4C are side, top, and perspective views, respectively, of a second embodiment of the optical fiber carrying tube utilized in the apparatus of the invention.

With reference now to FIGS. 3A–3C and 4A–4C, two separate embodiments for the remote end of either tube 12 or tube 32 are schematically illustrated. In FIGS. 3A–3C, it can be seen that the terminal end of tube 12 defines a conical shape with a blunt tip. The bundle of light-transmitting optical fibers 14 are contained within portion 12A thereof, and the bundle of light-receiving optical fibers 18 are contained within portion 12B of the terminal end of tube 12. An opaque or non-light-transmitting divider 12C is interposed between the light-transmitting and light-receiving optical fibers (preferably arranged in two optical fiber bundles). FIGS. 4A–4C depict a second embodiment of the terminal end of tube 12 wherein light-transmitting optical fibers 14 are contained within the concentric outer portion 12A and the light-receiving optical fibers 18 are contained within the center portion 12B of tube 12. Opaque divider 12C separates the light-transmitting and light-receiving optical fibers.

Common to both embodiments is that the terminal end of tube 12 defines a conical configuration so as to steer the photons from light-transmitting optical fibers 14 divergently away from light-receiving optical fibers 18 as best seen with reference to the photon pathways depicted in FIGS. 3A and 4A of the drawings. The optical principal of the divergent reflectance configuration is to increase the photon pathlength through the organ or tissue of interest so as to provide optical information from a more substantial volume of tissue and less backscatter of light from superficial tissue layers than would be acquired with a flat tube tip wherein the light-transmitting and light-receiving optical fiber bundles are in contiguous and parallel relationship. Applicants contemplate that the angle of the cone defined by the terminal end of tube 12 may be adjusted to provide a preferential signal from layers of tissue deep to the endocardial surface. Moreover, applicants contemplate that similar adjustments could be accomplished to optimize the volume of tissue sampled by applying suitable lenses (not shown) to the light-transmitting and/or light-receiving portions of the conical end of tube 12. By changing the pathlength of the photons by adjusting the conical angle or lens configuration thereon, it will be possible to allow the acquisition of optical metabolic information from different tissue depths. Similarly, the applicants contemplate the use of time domain multiplexing to allow for the selective reception of photons that have traversed different tissue depths.

Figure 5A:
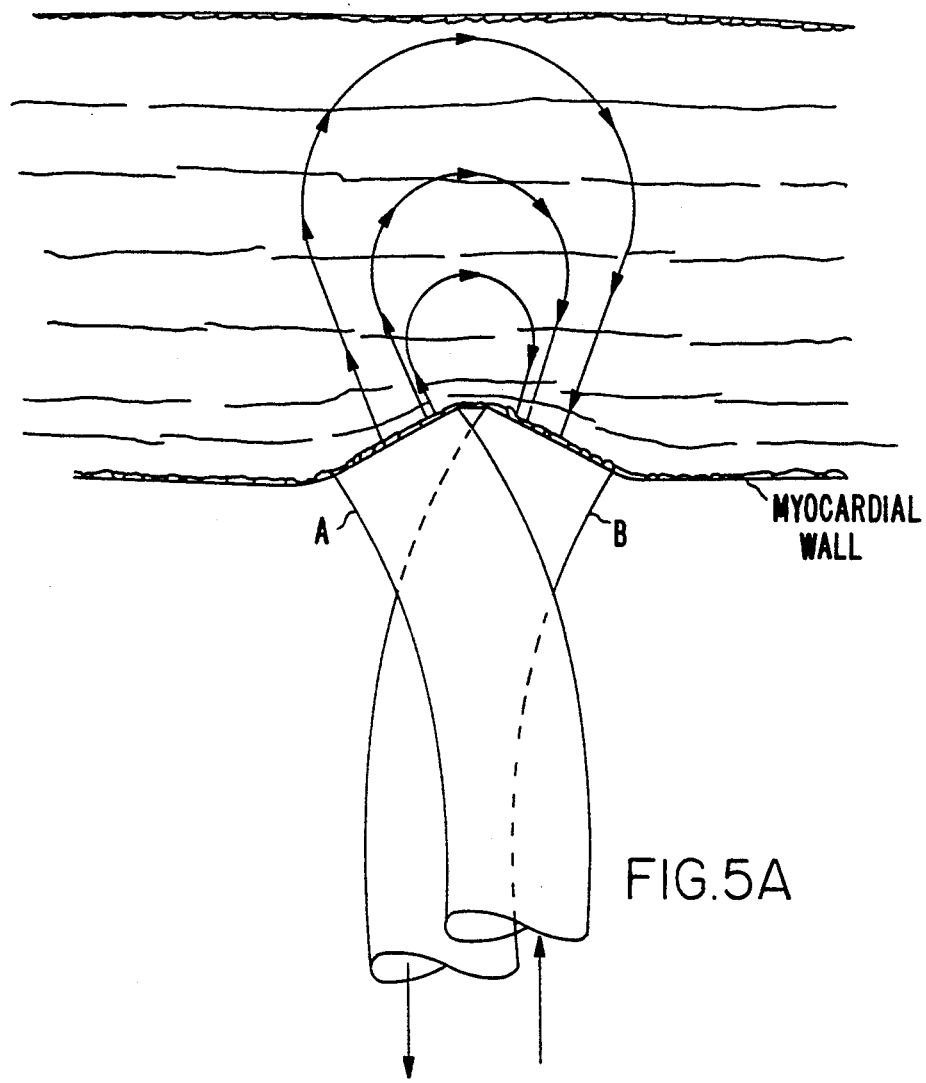
FIGS. 5A and 5B are a schematic side view showing an experimental optical fiber carrying tube constructed by applicants and a graphic representation showing results from testing thereof, respectively.
Figure 5B:
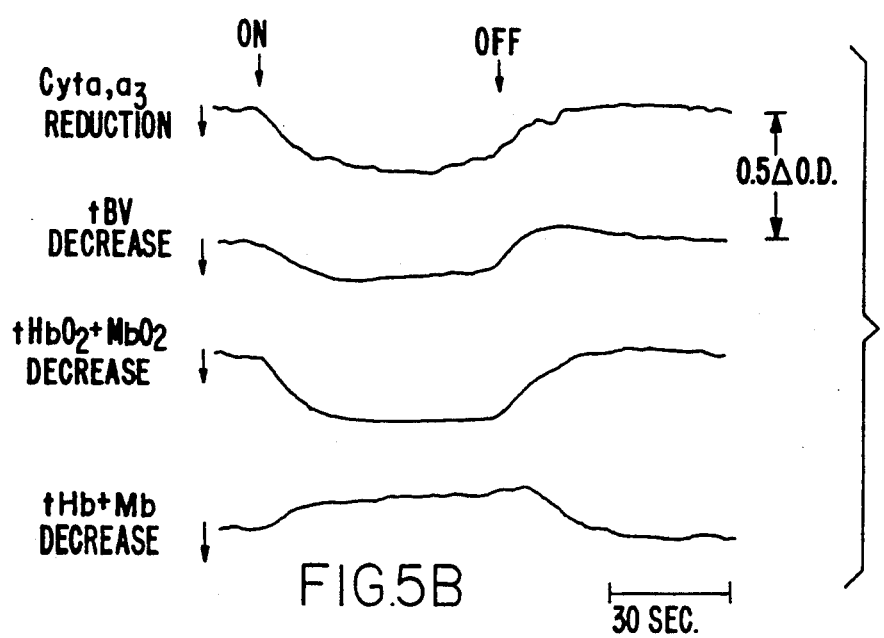

Applicants have experimentally tested the apparatus and method of the instant invention with the device shown in FIG. 5A of the drawings wherein two parallel fiber bundles are contiguous except at their terminal ends which are oriented in divergent relationship. Light-transmitting bundle A is oriented outwardly and away from light-receiving optical fiber bundle B. As can be seen with reference to the data shown in FIG. 5B, optical responses were acquired which are quite similar to optical responses acquired from cardiac tissue when the optical fiber bundles are spaced-apart by several centimeters and oriented parallel or convergently with respect to each other. Applicants believe that this test proves the efficacy of applicants' inventive method and apparatus to deliver and receive reflected near infrared (NIR) light from an endocardial region of interest to develop important optical information regarding regional oxidative metabolism including, but certainly not limited to, changes in the oxidation level of redox centers such as cytochrome a, $a_3$ copper and oxygenation of tissue hemoglobin and myoglobin. The tissue hemoglobin volume can also be assessed by addition of the hemoglobin plus myoglobin signals, assuming that myoglobin concentration remains constant (i.e., it remains in the optical field as either the oxy- or deoxyform), all of which can be monitored continuously in vivo by the percutaneous intravascular apparatus and method described herein.

In use, the steerable tip 12' of device 10 is delivered to the heart chamber via a percutaneous approach under fluoroscopic guidance and is then touched up against human or animal endocardium so as to permit optical coupling. Continuous or pulsed light from near infrared (NIR) light source 24 is transmitted along light-transmitting optical fibers 14 and delivered to the endocardium. The light traverses the tissue of interest and is received by the light-receiving optical fibers 18 and transmitted back through tube 12 to photodetector 26 for analysis. Although the data delivered by the reflected light may be analyzed in a variety of ways which are well known to those skilled in the art, applicants contemplate that a suitably programmed computer (not shown) could be placed in electrical connection with photodetector 26 in order to provide suitable analysis of the data carried by the reflected light.

ADVANTAGES OF THE INVENTION

The method and apparatus utilizing the divergent reflectance configuration described hereinabove enables the transmission and reception of near infrared (NIR) light for the measurement of important parameters of cardiac oxidative metabolism through a single fiber optic scope (catheter). By obviating the need for a second catheter in order to make the reflectance measurement, the invention provides a substantial advance over the prior art. Its advantages include the following:

1. Only one percutaneous (vascular access) site is required for admission of the scope into the intravascular space and advancement to the endocardial site of interest;

2. Since the light source and light receiver are delivered directly to an endocardial point of interest, there is no superficial structure through which the near infrared (NIR) light must pass (e.g., skin, bone, or skeletal muscle);

3. Since the light source and light receiver are delivered directly to an endocardial point of interest, the apparatus and method of the invention permit the acquisition of metabolic information from both diseased and normal sites and should therefore be of value in differentiating such regions in living persons. The potential capacity to discern regional viability and the metabolic effects of available blood flow within abnormally contracting heart segments may affect clinical decisions regarding the need for therapeutic intervention such as thrombolysis, balloon angioplasty, and coronary artery bypass grafting;

4. The apparatus and method of the invention may be used in a standard clinical cardiac catheterization laboratory and may be done as part of a routine diagnostic catheterization study in human beings; and 5. The method described herein is substantially less expensive than non-optical methods of accessing regional cardiac metabolism in human beings such as PET (position emission tomography) or NMR (nuclear magnetic resonance) spectroscopy.

Finally, applicants wish to note that while intravascular measurement of myocardial metabolism has been described in detail herein, it is contemplated that the apparatus and method of the invention could be utilized in other ways and are not restricted in any fashion merely to intravascular measurement of myocardial metabolism. For example, the apparatus of the invention could be advanced down the esophagus and the conical tip thereof directed against the esophageal wall toward the adjacent cardiac muscle. The apparatus could also be advanced via any physiologic conduit within the human body of ample dimension to admit a tube or scope of the dimensions described hereinabove, including a vascular conduit, the urinary tract, within the biliary tree, within the gastrointestinal tract, and the like to permit similar measurements of oxidative metabolism and blood volume in organs and tissues of interest such as the heart, brain, liver, kidney, and sketetal muscle. Moreover, although the apparatus and method of the invention have been described hereinabove in terms of using near infrared (NIR) light to acquire metabolic information, applicants contemplate that the invention could also utilize visible or near ultraviolet wavelengths of light, and that the use thereof is within the scope of the instant invention. Also, although the device of the invention is described as utilizing a plurality of optical fibers for both the sending and receiving function, applicants contemplate that as few as one optical fiber could be used in the tube of scope 12 for each function.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of measuring oxygen availability and utilization in internal body organs such as the heart, brain, liver and kidneys or selected body tissue, comprising the steps of:
    providing a tube containing a plurality of optical fibers and comprising at least one light-transmitting optical fiber having a proximal and distal end and at least one light-receiving optical fiber having a proximal and distal end wherein said distal ends of said at least one light-transmitting optical fiber and said at least one light-receiving optical fiber are divergently oriented relative to each other;
    inserting said tube through at least a portion of the length of a body conduit and into contact with an organ or tissue of interest;
    directing light into the proximal end of said at least one light-transmitting optical fiber so as to transmit said light therethrough and out of the distal end thereof into said organ or tissue of interest in a direction divergent from the distal end of said at least one light-receiving optical fiber;
    receiving reflected light which has traversed a portion of said organ or tissue of interest in the distal end of said at least one light-receiving optical fiber so as to transmit said reflected light therethrough and back to the proximal end thereof; and
    analyzing said reflected light to obtain measurements of oxidative metabolism and/or related data for the organ or tissue of interest.

2. A method as defined in claim 1 wherein said light is near infrared (NIR) light.

3. A method as defined in claim 1 wherein said light is visible light.

4. A method as defined in claim 1 wherein said light is near ultraviolet light.

5. A method as defined in claim 1 wherein oxygen availability and utilization in the heart is measured by inserting said tube via a percutaneous, intravascular route to an endocardial point of contact within the heart.

6. A method as defined in claim 5 wherein said measurements of oxidative metabolism and related data include changes in the oxidation level of cytochrome a, $a_3$ copper, oxygenation of tissue hemoglobin and myoglobin, and tissue blood volume.

7. A method for measuring oxygen availability and utilization in internal body organs such as the heart, brain, liver and kidneys or selected body tissue, comprising the steps of:
    providing a tube containing a plurality of optical fibers and comprising at least one light-transmitting optical fiber having a proximal and distal end and at least one light-receiving optical fiber having a proximal and distal end wherein said distal ends of said at least one light-transmitting optical fiber and said at least one light-receiving optical fiber are adapted to transmit and receive light, respectively, along divergent pathways;
    inserting said tube through at least a portion of the length of a body conduit and into contact with an organ or tissue of interest;
    directing light into the proximal end of said at least one light-transmitting optical fiber so as to transmit said light therethrough and out of the distal end thereof into said organ or tissue of interest in a direction divergent from the distal end of said at least one light-receiving optical fiber;
    receiving reflected light which has traversed a portion of said organ or tissue of interest in the distal end of said at least one light-receiving optical fiber so as to transmit said reflected light therethrough and back to the proximal end thereof; and
    analyzing said reflected light to obtain measurements of oxidative metabolism and/or related data for the organ or tissue of interest.

8. A method as defined in claim 7 wherein said light is near infrared (NIR) light.

9. A method as defined in claim 7 wherein said light is visible light.

10. A method as defined in claim 7 wherein said light is near ultraviolet light.

11. A method as defined in claim 7 wherein oxygen availability and utilization in the heart is measured by inserting said tube via a percutaneous, intravascular route to an endocardial point of contact within the heart.

12. A method as defined in claim 11 wherein said measurements of oxidative metabolism and related data include changes in the oxidation level of cytochrome a, $a_3$ copper, oxygenation of tissue hemoglobin and myoglobin, and tissue blood volume.

* * * * *